United States Patent [19]

Phalangas

[11] Patent Number: 5,112,886

[45] Date of Patent: May 12, 1992

[54] ALLANTOIN SALTS OF QUATERNARY NITROGEN CONTAINING POLYMERS FOR USE IN SKIN CONDITIONING, COSMETIC AND PHARMACEUTICAL FORMULATIONS

[75] Inventor: Charalambos J. Phalangas, Wilmington, Del.

[73] Assignee: ICI Americas Inc., Wilmington, Del.

[21] Appl. No.: 334,968

[22] Filed: Apr. 7, 1989

Related U.S. Application Data

[63] Continuation of Ser. No. 911,747, Sep. 26, 1986, abandoned.

[51] Int. Cl.$^5$ .................................................. C08K 0/00
[52] U.S. Cl. .................................... 523/332; 524/547; 524/555; 524/557; 524/815; 525/61; 525/375
[58] Field of Search ............... 524/557, 547, 555, 815; 525/61, 375; 523/332

[56] References Cited

U.S. PATENT DOCUMENTS

| | | | |
|---|---|---|---|
| 4,293,654 | 10/1981 | Levine et al. ..................... | 525/61 X |
| 4,374,766 | 2/1983 | Puchalski et al. ............... | 424/177 X |
| 4,482,537 | 11/1984 | El-Menshawy et al. ............. | 424/59 |
| 4,645,794 | 2/1987 | Davis et al. ........................ | 525/61 |

*Primary Examiner*—Joseph L. Schofer
*Assistant Examiner*—J. M. Reddick
*Attorney, Agent, or Firm*—William E. Dickheiser

[57] ABSTRACT

Polymers having pendent cationic quaternary nitrogen containing groups form salts with allantoin which provide for a film forming moisture barrier in skin conditioning lotions, ointments, cosmetics conditioning treatments, and pharmaceutical formulations.

17 Claims, No Drawings

ALLANTOIN SALTS OF QUATERNARY NITROGEN CONTAINING POLYMERS FOR USE IN SKIN CONDITIONING, COSMETIC AND PHARMACEUTICAL FORMULATIONS

This is a continuation of co-pending application Ser. No. 911,747, filed Sep. 26, 1986, now abandoned.

The present invention is directed to conditioning polymers which when applied to skin form coatings or thin films which aid in healing and reduce moisture loss. The invention relates in general to polymers and copolymer derivatives and specifically to those having cationic quaternary nitrogen containing pendent groups and allantoin anions. Of particular interest are polymers having a preformed polyvinyl alcohol backbone or base chain with pendent substituent quaternary ammonium groups randomly attached through various linkages to the chain. Such base chains of quaternary ammonium groups provide a multiplicity of cationic sites which form salts when mixed with allantoin ($C_4H_5N_4O_3^-$) anions The invention is further directed to a method for making these compounds as well as the formulations containing them.

Allantoin has long been recognized for its skin moisturizing, healing, anti-irritant, and keratolitic properties. Because of these beneficial properties, it has been added to many skin care and cosmetic formulations. However, its incorporation in these formulations is restricted by its low solubility in water. As a result, a number of allantoin complexes are used to overcome this deficiency, such as aluminum chlorohydroxy-allantoinate (A.S. Alcoxa), allantoin polygalucturomic acid (Alpolygal), allantoin proteins (Alpro) etc.

Allantoin is slightly soluble in water (0.5% at 25° C.) and has the empirical formula $C_4H_6N_4O_3$. In saturated aqueous solution it has a pH of about 4-6. It is effective in cleansing, healing and soothing without irritation or sensitization of open wounds and skin tissue. Furthermore it promotes the growth of cells of new and healthy tissue.

Allantoin is known to exist in a keto and enol form in equilibrium. The enol form acts as a weak acid forming true salts with cations such as amine solutions and quaternary ammonium bases. These allantoin salts exhibit higher solubility in water than allantoin. I have found that amine and ammonium nitrogen bearing polymers form stable polysalts with allantoin which have considerable solubility in water and do not separate.

The importance of this finding lies in the fact that many of these amine and ammonium nitrogen bearing polymers may now be used in skin care and cosmetic formulations as skin moisturizers or skin moisture barriers preventing skin dehydration; in hair care and grooming formulations and shampoos; in shaving creams and lotions; in pharmaceutical formulations, ointments, burn lotions and in other wound dressings, spray-on bandages, etc.

The allantoin salts with polycationic polymers combine the moisturizing and/or skin moisture barrier properties of these polymers with the moisturizing, keratolytic, anti-irritant and healing properties of allantoin. As such, they have a greater beneficial effect on the skin or hair than either the polymers alone or prior art allantoin salts. Of particular interest and utility are salts of allantoin with certain film forming cationic polymers having controlled levels of hydrophilic and lipophilic balance. These products, when added to skin care, cosmetic or pharmaceutical formulations, leave a thin film which adheres to the skin and protects it from dehydration, exhibit durability to fresh water wash off and allow allantoin to be released at a rate proportionate to their hydrophilic/lipophilic balance. The sustained release of allantoin on the skin along with the prevention of dehydration due to durable polymeric film maintains a satisfactory level of moisture while controlling skin irritation. Furthermore, these properties are very beneficial in the transdermal delivery of drugs. It has been recognized that the rate of drug penetration through the skin from drug loaded epidermal patches depends on the moisture level of the Stratum corneum. Therefore, the dose of a specified drug delivered to an individual varies with the history of the skin, season of the year, time of the day, exposure to sun or wind, etc. The use of these allantoin containing polymers for the preparation of semipermiable membranes or in conjunction with such membranes for the controlled transdermal delivery of drugs can maintain a constant level of moisture in the Stratum corneum under an epidermal patch and provide for a consistent penetration rate through the skin independent of skin history and exposure.

It is an object of the invention to provide for quaternary nitrogen containing polymer chains (having a number average molecular weight of at least 2,000 and preferably up to about 200,000 and up to 1 million when unmodified) having in a random or ordered distribution a multiplicity of pendent groups having general formula: $-RN^+R_1R_2R_3A^-$ wherein R is an alkylene, alkyl substituted alkylene, hydroxy alkylene, oxylinked alkylene such as ether or acylene linked, sulfur linked, or nitrogen linked wherein said total substituent has a formula weight ranging from 14 to about 3,000; $R_1R_2R_3$ are selected from alkyl, arylalkyl radicals having 1-22 carbon atoms which may be the same or different, and hydrogen; $A^-$ is an anion selected from allantoin ($C_4H_5N_4O_3^-$) and derivatives thereof.

The quaternary ammonium resin is made by either treating the active base resins with a quaternary ammonium or an amine containing group and linked therewith through metathesis or by polymerizing an amine or quaternary ammonium containing ethylynically unsaturated monomer to form the base chain. The base chain may have oxygen atoms linked at alternate or random carbons and may be formed by copolymerizing ethylene, propylene, butylene, vinyl acetate, vinyl chloride, vinyl esters and esters of acrylic and methacrylic acid and thereafter reacting said chain with quaternizing groups to form a quaternary ammonium resin containing from about 0.01-3% by weight nitrogen. Another method for forming the base chain is to polymerize ethylenically unsaturated amines or quaternary ammonium materials to form the base resin.

In addition to the pendent quaternary ammonium groups linked to the base chain may be linked lipophilic and hydrophilic groups. Therefore the carbon-carbon base chain may contain a variety of additional substituents comprising alkyl, aryl, hydroxyl, carboxyl, carboxyester, keto, acetyl, halo, mercapto and the like linked therewith in an equivalent or minor proportion and which have a variety of chemical and physical properties.

The allantoin salts are simply made by comixing an aqueous slurry of allantoin or allantoin salts and quaternized resin to form solutions, emulsions or solid resin particles having linked therewith the quaternary ammonium allantoin salt.

Polyallantoin salts of the present invention can be theoretically described but not limited to the nine general structures in the following table:
Table of Structures
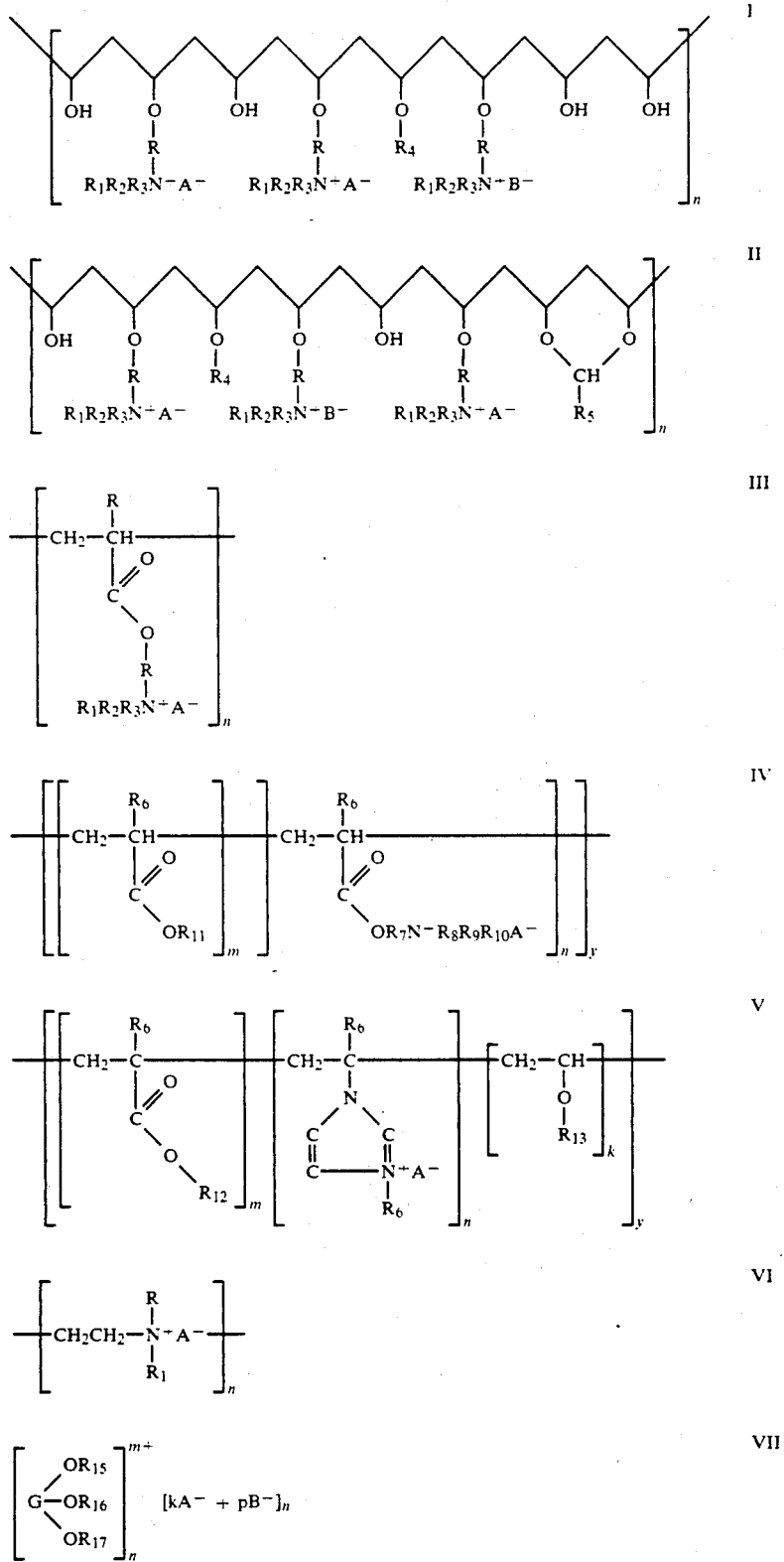

Table of Structures
-continued

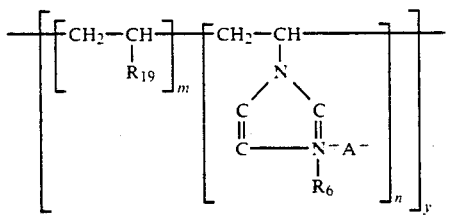    VIII

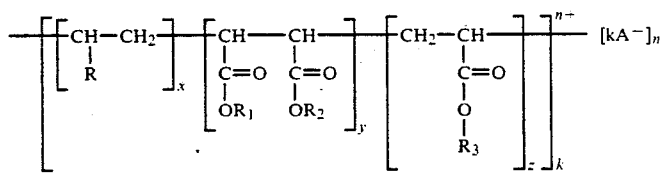    IX

In formula I, R is alkylene, acyl, arylalkylene, or substituted alkylene, acyl or arylalkylene. $R_1$, $R_2$, $R_3$, $R_4$, can be independently hydrogen, alkyls, arylalkyl, cycloalkyls or substituted alkyl, cycloalkyls and alkylaryls, $A^-$ is allantoin anion, $B^-$ is one or more optional anions, n is an integer. $n[A^-] \geq 1$, and $n[B^-] \geq 0$.

In formulas II, III, IV, and V, R, $R_1$, $R_2$, $R_3$, $R_4$, $A^-$ and $B^-$ are as before and $R_5$ is alky, aryl, alkylaryl or substituted alkyl, aryl or alkylaryl, and n is an integer.

$R_6$ is hydrogen, arkyl, substituted alkyl $R_7$ is Alkylene or akyl substituted alkylene radical.

$R_8$, $R_9$, $R_{10}$ are independently selected from H, alkyl substituted alkyl, aryl or alkylaryl radical.

where m, n, y are integers having values: m=0-50n; n≥1; y≥1.

$R_{11}$=alkyl aryl, aralkyl, cycloalkyl with 1-22 carbon atoms.

$R_6$ is independently hydrogen, alkyl, arylalkyl, cycloalkyl or substituted alkyl, arylalkyl and cycloalkyl $R_{12}$ is alkyl, arylalkyl, cycloalkyl or $-R_{14}N^+R_5R_6R_7A^-$ where $R_{14}$ is an alkylene, arylalkylene radical and $R_5$, $R_6$, $R_7$ are independently hydrogen alkyl, arylalkyl, cycloakyl or substituted akyl, arylalkyl and cycloalkyl $R_{13}$ is alkyl, acyl arylalkyl or cycloalkyl or $-R_{14}R_5R_6R_7N^+A^-$ the m, n, k and y are integers, m≥0; k≥0; n≥0; m+n+k≥1; y≥1; $[A^-]1 \geq 1$.

In formula VI R, $R_1$ and $A^-$ are as described above.

In formula VII $A^-$ and $B^-$ are as described above where:

n, m, k and p are integers with k, n, m>1; m=k+p; n is 10-25,000. G is an anhydroglucose residue.

$R_{15}$, $R_{16}$, $R_{17}$ independently are:

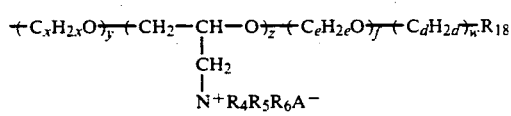

where x, y, z, e, f, d and w are integers with the following values:
x=2-3; y=0-20; z=0-5; e=2-3; f=0-20; d=1-3; w=0-1.
$R_{18}$=—H,

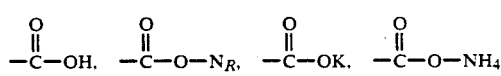

$R_4$, $R_5$, $R_6$=alkyl aryl aralkyl cycloakyl or substituted alkyl, aralkyl and cycloalkyl radicals with 1-22 carbon atoms.

In formula VIII, m, n and y are integers $R_{19}$ is selected from Hydrogen, alkyl, $-OR_3$, $R_4COO-$, $R_5-NH-COO-$.

$R_3$, $R_4$, $R_5$ are selected from alkyls or aryls with 1-22 carbon atoms.

In formula IX, R is selected from hydrogen, hydroxyl, alkyl, aryl, alkylaryl and the groups

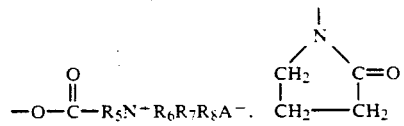

where $R_5$ is alkylene or arylalkylene $R_6$, $R_7$ and $R_8$ are independently hydrogen, alkyl, arylalkyl cycloalkyl or substituted alkyl, alkylaryl or cycloalkyl. $R_1$, $R_2$, $R_3$ are independently hydrogen, alkyl, arylalkyl cycloalkyl or $-R_5N^+R_6R_7R_8$ where $R_5$, $R_6$, $R_7$ a are the same as before.

x, y, z, n and k are integers having values x, y, z, ≥0; (x+y+z)≥1; k, n≥1.

The quaternary nitrogen containing polyvinyl alcohol polymer compositions of the invention may be represented by a typical polymer segment having the following idealized structural formula:

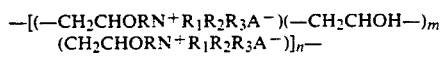

where
n=20-3000; and m=0-600; and R, $R_1$, $R_2$, $R_3$, and $A^-$ are the same as described above.

Illustrative of the other types of numerous pendent quaternary groups linked by oxygen as randomly distributed units in the polyvinyl alcohol base chain may be given as follows:

  (1)

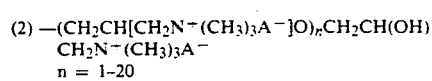

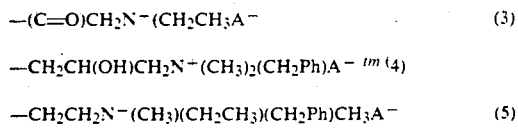

$-(C=O)CH_2N^+(CH_2CH_3)_3A^-$ (3)

$-CH_2CH(OH)CH_2N^+(CH_3)_2(CH_2Ph)A^-$ (4)

$-CH_2CH_2N^+(CH_3)(CH_2CH_3)(CH_2Ph)CH_3A^-$ (5)

where Ph=phenyl.

While the above structures serve to illustrate the types of pendent quaternary ammonium groups which can be added to the polyvinyl alcohol base chain it is apparent to one skilled in the art that many other arrangements of similar chemical structure can be incorporated. It has been found that each of the above types of groups used alone or in combination with one or more of the others as a substituent on the polyvinyl alcohol base chain yields the desired combination of products having useful moisture barrier properties especially when the nitrogen content of the final product ranges from 0.01%-5% and preferably 0.01-3% by weight. Depending on the type of radical attached to the nitrogen of the quaternary group the effective range of the nitrogen content could be even more specific. It has been found for example that when the $R_1$, $R_2$, $R_3$, in the above general formulas are all methyl radicals the effective nitrogen content may range from 0.1-3% by weight.

PREPARATION OF QUATERNIZED RESIN

General Preparation I

A flask equipped with a water cooled condenser, mechanical stirrer and thermometer is charged with polyvinyl alcohol and distilled water. The polyvinyl alcohol (PVA) which is generally a commercially available product prepared by hydrolysis of polyvinyl acetate may have from 0 to 25% residual acetate groups, preferably from 0.2 to 15% and the number average molecular weight may range from 2,000 to 200,000 and higher and preferably from 10,000 to 150,000. In addition, and for the purpose of this invention, a polyvinyl alcohol base chain may include up to 25% by weight of another comonomer such as vinyl pyrolidone, acrylic and methacrylic acids and esters thereof The aqueous slurry is heated to 80°-90° C. and held for 1 hour or until the polyvinyl alcohol is completely dispersed or solvated. A catalytic amount of aqueous base such as alkali hydroxide such as sodium or potassium hydroxide is then added and the solution cooled to 40°-90° C. At this point 2,3-epoxypropyltrialkylammonium halide, either in aqueous solution or crystalline form, may be added incrementally or all at once. This reagent is typically used in 0.003-1.0 mol ratio preferably from 0.10-0.3 mol per mol of hydroxyl group on the polyvinyl alcohol base chain. The entire solution is then stirred for an additional period typically 4 hours at 60° C. after which the product may be recovered.

Recovery is accomplished by one of two general techniques. The solution can be poured into a polymer non-solvent to precipitate solid product from aqueous solution. Alternatively the solution may be dialyzed through a semiporous membrane and the purified aqueous polymer used as obtained or precipitated out.

The precipitation is preferably accomplished either in acetone or in methanol affording yields up to 90% or better by weight after drying. Depending on reaction conditions the precipitated products have a nitrogen content in the range of 0.01-7%.

In the purification by dialysis the reaction mixture is freed from all species below a certain molecular weight. Two methods may be used one a static and one dynamic. In the static method the reaction mixture is placed inside commercial semiporous dialysis tubes and the tubes are submerged in distilled water typically for periods of 12 to 48 hours. The contents of the tubes are then recovered and the product may be used as is. In the dynamic system a pressure pump is used to move water from the reaction mixture through a semi-pourous membrane. The water carries out any inorganics and low molecular weight organics. The resulting concentrated product stream is then collected.

The following examples and preparations serve to illustrate but not limit the invention. All proportions used refer to parts by weight unless otherwise specified.

Preparation A (Chlorohydroxypropyl)trimethylammonium chloride

A one-liter flask equipped with dropping funnel, mechanical stirrer thermometer and condenser was charged with epichlorohydrin (95 grams, 1.02 mol) and placed in an isothermal bath at 18° C. Aqueous trimethylamine (238.7 grams, 25% by weight, 1.01 mol) was then added dropwise over a 3 hour period maintaining the temperature below 25° C. when the addition was complete the solution was allowed to stir overnight at ambient temperature.

Preparation 1

$-RN^+R_1R_2R_3A^- = -CH_2-CH(OH)CH_2N(CH_3)_3Cl$

A flask equipped as described in General Preparation I was charged with 44 grams polyvinyl alcohol (commercially available) having a molecular weight of 126,000 (98% hydrolyzed - 2% acetate) and 400 milliliters of distilled water. The resulting slurry was heated to 85° C. and held for 1 hour. The polymer dissolved completely to afford a pale yellow transparent solution. Potassium hydroxide (3.0 gram, 0.11 mol) in water (30 milliliters) was then added and the solution cooled to 60° C. Aqueous (chlorohydroxypropyl)trimethylammonium chloride (78 milliliters of 48% by weight aqueous solution prepared according to Preparation A), was then added all at once and the entire solution was heated to 60°-65° C. for 4 additional hours. The warm solution was poured with stirring into acetone (2.0 liters) and allowed to stand. 63.5 grams of colorless solid precipitate was collected by filtration shredded mechanically and dried under vacuum. The nitrogen content of the product was 2.15% by weight wherein the value for (m) in the above general formula segment is approximately 21.

Preparation B

Crystalline 2,3-epoxypropyltrimethylammonium chloride

A one-liter flask equipped with was gas sparger, mechanical stirrer, thermometer and an aqueous acid trap was charged with epichlorohydrin (552 grams, 6.0 mol) and placed in an isothermal bath at 19° C. Trimethylamine gas (119.5 grams, 2.0 mol) was then sparged into the epichlorohydrin over a period of 3 hours. The temperature was maintained below 23° C. The solution was stirred for an additional 30 minutes and the precipitate collected by filtration. The crystalline product was washed with diethylether and vacuum dried to afford 262.2 grams of 2,3-epoxypropyltri-methylammonium chloride.

Preparation 2

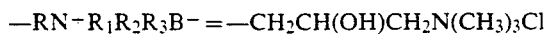
—RN⁻R₁R₂R₃B⁻ = —CH₂CH(OH)CH₂N(CH₃)₃Cl

The procedure of Preparation 1 was repeated exactly except that pure crystalline 2,3-epoxypropyltrimethylammonium chloride (15.2 grams, 0.10 mol) of Preparation B was added in place of the aqueous solution. The mixture was then stirred for an additional 5.5 hours at 60° C. and recovered from acetone as described. The nitrogen content of the final product was 1.12% by weight wherein the value for (m) is approximately 28.

Preparation 3

—RN⁺R₁R₂R₃B⁻ = —CH₂CH(OH)CH₂N(CH₃)₃Cl

The procedure of Preparation 1 was reproduced except that the amount of aqueous 2,3-epoxypropyltrimethylammonium chloride was 56.2 milliliters of 48% solution and the warm aqueous polymer was recovered by precipitation in methanol (2.0 liters). The solid collected was shredded mechanically dried under vacuum and milled to a fine powder. The yield was 49.9 grams and the nitrogen content was 0.22% by weight.

Preparation 4

—RN⁻R₁R₂R₃B⁻ = —CH₂CH(OH)CH₂N(CH₃)₃Cl

The procedure of Preparation 3 was reproduced with the exception that the aqueous reaction mixture was cooled to ambient temperature and placed in a commercially available dialysis tube. The semiporeous membrane in the dialysis tube retains all molecules with molecular weights greater than 8,000. The tubes were placed in water (4 liters) and allowed to stand. The bath water was changed ever 6–8 hours over a 36 hour period. The tubes were then recovered and the aqueous polymer solution inside was tested for moisture barrier properties.

Preparation 5

—RN⁺R₁R₂R₃B⁻ = —CH₂CH(OH)CH₂N(CH₃)₃Cl

The procedure of Preparation 3 was reproduced with the exception that recovery was accomplished by precipitation from acetone (1.5 liters). The scale was slightly reduced to 38.0 grams polyvinyl alcohol and 49 milliliters of 48% aqueous epoxide solution. The yield was 63.5 grams and the nitrogen content was 2.63% by weight wherein the value for (m) in the general formula segment is approximately 15.

Preparation C

Preparation of 2,3-epoxypropyltrimethylammonium bromide

A flask equipped with a sparger, mechanical stirrer, thermometer and efficiency condenser was charged with acetone (500 milliliters) at ambient temperature. Trimethylamine (58 grams, 0.98 mol) was charged into the solution. The pot was cooled to 10° C. and epibromohydrin (137 grams, 1.0 mol) was added dropwise over a 1 hour period. The resultant cloudy solution was allowed to slowly rise to ambient temperature and stand for 60 hours. Precipitate was collected by filtration washed with acetone (60 milliliters) and dried yielding a colorless crystalline product (179.4 grams, 94%).

Preparation 6

—RN⁻R₁R₂R₃B⁻ = —CH₂CH(OH)CH₂N(CH₃)₃Br

A flask equipped as described in General Preparation I was charged with polyvinyl alcohol (44.0 grams), (98% hydrolyzed, number average molecular weight equals 126,000) and 500 milliliters water. The slurry was warmed to 70° C. and potassium hydroxide (3.0 grams) was added. The pot was stirred an additional 30 minutes and 2,3-epoxypropyltrimethylammonium bromide (49.0 grams, 0.25 moles) was added through a powder funnel. This solution was stirred for 16 hours at 80° C. The solution was then poured into acetone (1500 milliliters) and the precipitate was collected by filtration, shredded, washed and dried. The pale brown solid powder which resulted had a nitrogen content tent of 2.10% by weight wherein the value for (m) in the general formula segment is approximately 19.

Preparation 7

—RN⁺R₁R₂R₃B⁻ = —CH₂CH(OH)CH₂N⁺(CH₃)₃Cl

A flask equipped as described in General Preparation I was charged with polyvinyl alcohol (44.0 grams), (100% hydrolyzed, number average molecular weight equals 86,000), 200 milliliters distilled water and 3 grams potassium hydroxide. The pot was heated to 60° C. an aqueous (chlorohydroxypropyl)trimethylammonium chloride (320 milliliters, 48% aqueous solution as prepared in Preparation A) was added. Heating was continued for an additional 24 hours and recovery was accomplished by precipitation from acetone. After collection washing and drying the nitrogen content was 0.72% wherein the value for (m) in the general formula segment is approximately 80.

Preparation 8

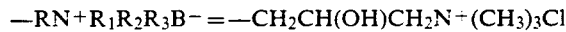
—RN⁺R₁R₂R₃B⁻ = —CH₂CH(OH)CH₂N⁺(CH₃)₃Cl

A flask equipped as described in General Preparation I was charged with polyvinyl alcohol (88.0 grams), (98.5% hydrolyzed, having a molecular weight of 25,000) and 800 milliliters of water. The reaction was carried out exactly as described in Example 2 using crystalline 2,3-epoxypropyltrimethylammonium chloride (79.6 grams). Recovery was accomplished by precipitation in acetone. The nitrogen content was 1.01% by weight wherein the value for (m) in the general formula segment is approximately 84.

Preparation 9

—RN₊R₁R₂R₃B⁻ = —COCH₂N⁺(CH₃)₂(CH₂Ph)Cl

A flask equipped as described in General Preparation II was charged with polyvinyl alcohol (44.0 grams), (100% hydrolyzed, molecular weight 86,000), 500 milliliters dimethylformamide, 5.5 grams maganese acetate, and benzyldimethylethoxycarbonymethyl ammonium chloride (51.0 grams, 0.25 mole). A nitrogen stream was passed through the solution as was heated to 125° C. and held for 6 hours. The resulting solution was poured into acetone (1500 milliliters) while hot. The precipitate was collected by filtration, shredded mechanically, washed again with polymer non-solvent and dried. The product was found to have a chloride content of 4.10% by weight and a calculated nitrogen content of 1.62% wherein the value for (m) in the general formula segment is approximately 28.

Preparation 10

The process of Preparation 9 was repeated with polyvinyl alcohol (98% hydrolyzed having molecular weight of 126,000). The chloride content of the product was 4.41% by weight and the calculated nitrogen content was 1.72% wherein the value for (m) in the general formula segment is approximately 25.

Preparation 11

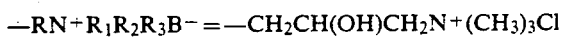

Polyvinyl alcohol (44.0 g, MW=126,000, 98% hydrolyzed) was stirred in water (400 ml) and warmed to 85°-90° C. The solution was cooled to 80° C. and aqueous potassium hydroxide (5.6 g in 30 ml H$_2$O) was added. This solution was cooled over 30 minutes to 60° C. and (3-chloro-2-hydroxypropyl)trimethylammonium chloride (18.8 g, 0.10 mol) was added all at once. The pH at this time was 7.3. The product was recovered by dialysis through a semi-porous membrane as previously described. The nitrogen content was 0.15% which corresponds to idealized formula with m=415.

Preparation 12

Polyvinyl alcohol (22.0 g), (MW=126,000, 98% hydrolyzed) was stirred in water (210 ml) and warmed to 85° C. over 45 minutes. Potassium hydroxide (1.5 g in 10 m H$_2$O) was then added and the solution cooled to 60° C. Crystalline 2,3-epoxy-propyltrimethylammonium chloride (75.8 g, 0.50 mol) was added and the entire solution held at 60° C. for 4 hours. The product was then recovered by precipitation from acetone, filtration and drying to afford 102 grams of white powder. The nitrogen content was 5.96% or 88% of theoretical, and wherein (m) has a value of approximately 2.0.

Preparation 13

Polyvinyl alcohol (44.0 g), (MW=126,000, 98% hydrolyzed) was stirred in water (400 ml) and warmed to 85° C. over 30 minutes. The solution was cooled to 80° C. and Potassium hydroxide (3.0 g in 20 ml H$_2$O) was added. The entire solution was cooled to 60° C. over 45 minutes and 2,3-epoxypropyltrimethylammonium chloride (37.9 g in 100 ml H$_2$O) was added dropwise over 30 minutes. The solution was stirred at 60° C. for 3 additional hours and the product recovered by precipitation from acetone. The reaction afforded 50.4 grams of white solid with a nitrogen content of 2.92% or 71% of theoretical, and wherein (m) has a value of approximately 13.

GENERAL PREPARATION OF SALTS

The products of the invention are made by combining the above described modified PVA resin starting materials with allantoin to form quaternary ammonium/allantoin salts. In general the PVA resin is dispersed in water, adjusted to a pH of 6-10 and thereafter mixed with from 0.5-25% by weight based on the weight of the resin of allantoin derivative or allantoin salt.

The following examples serve to illustrate but not limit the invention wherein all proportions express or base on weight unless otherwise specified.

EXAMPLE 1

Into a 100 gallon glass lined vessel equipped with anchor agitator were charged 46.25 lbs of medium viscosity PVA, Vinol ® 125, a product of Air Products and Chemicals and 213.5 lbs of deionized water. The mixture was heated to 95° C. under constant stirring and maintained at this temperature until all the PVA was dissolved. The solution was then cooled to 60°-65° C.

In a separate vessel a KOH solution was prepared by dissolving 6.64 lbs of 87% KOH in 19.8 lbs of water. The KOH solution was slowly added to the constantly stirred PVA solution the temperature of which was maintained at 60°-65° C. After all KOH solution was added, the PVA solution was maintained for one additional hour at 60°-65° C. under constant stirring. Subsequently 20.7 lbs of 3-chloro-2-hydroxypropyltrimethylammonium chloride was added as a 60% aqueous solution and the reaction mass was maintained at 60°-65° C. for 3.5 hr under stirring.

At the end of the 3.5 hr period, a hydrochloric acid solution, made by dissolving 3.86 lbs of 35% HCl in 11.7 lbs of water, was added to the reaction mass, the pH of which was brought to about 7.0. To the neutralized reaction mass 147 lbs of water were added and mixed well. The diluted raw product was then filtered through a 100 micron filter and processed through an ultrafiltration unit until 95% of all low molecular weight species were removed. The purified product contained 10% quaternized PVA and 90% water.

To 3.0 kg of the of purified product, a solution of 2.5 g of KOH in 7.5 g of water was added which brought the pH to 12.0. 60 g of allantoin were added to this solution at 25° C. and the product was brought to 55° C. under stirring. A slightly hazy solution resulted having pH=7.0. 400 g of additional purified 10% quaternized PVA solution were added and the solution became clear. H$_3$PO$_4$ was added to the clear solution to adjust its pH to 5.0. To this solution 36 g of Germaben II ® were added and mixed well. The final product was cooled to room temperature and remained a colorless and clear solution with a turbidity of 12 nephelometer units. Its composition was 10% quaternized PVA having a 0.3% nitrogen content, a 1.7% allantoin and 1% Germaben II ® with the balance water.

EXAMPLE 2

A 500 ml resin reactor fitted with an anchor agitator, N$_2$ sparge, reflux condenser and thermometer was charged with 125 gms PVA, 312.5 gms t-butyral and 17.0 gms sodium hydroxide in 62.5 gms distilled H$_2$O. Nitrogen was sparged for 1 hour at 100 ml/min. while heating to 60°-65° C. 94 gms of Dowquat ® 188, a product of Dow Chemical Corp., in 37.6 gms H$_2$O were added over 2 hrs. at 60°-65° C. The reaction was then filtered and washed with the OH and cold water. The filter cake was then dried in a vacuum over night. Analysis: % N =0.66.

10 gms of the above quaternized polyvinyl alcohol having a % N of 0.66 was added to 90 gms of distilled H$_2$O while warming on a hot plate to 50° C. Resulting mix was a clear light yellow with a pH of 10-12 with paper. To this mixture was added 2 gms of allantoin CP (2% by wt) and stirred til clear. It had a pH of 7-8.

EXAMPLE 3

A quaternized resin was prepared in the same manner as in Example 1 and had a N$_2$ content of 0.68%. To 100 g of 10% dispersion 3 gms of allantoin CP (3% by wt) was added. The pH of the dispersion was 6-7.

Both of the dispersions of Example 2 and Example 3 were allowed to sit at room temperature over night. The dispersion with 2% allantoin remained clear. The solution with 3% allantoin remained clear with some precipitation of the allantoin.

The problems associated with employing either allantoin or unmodified PVA in film forming bases are substantially overcome by the compositions of this invention in that they are easily dispersible in water, are compatible with typical lotion formulations, and when applied to the surface of the skin, they dry quickly to form an elastic, smooth pellicle which retains its integrity over long periods of time which is easily removed with soap and water. Tests for pharmaceutical elegance is accomplished by applying typical moisture barrier lotion formulas to the back of the hand and making observations with respect to ease of application, feel on the skin, time of drying, durability of the film, ease of removal and a host of subjective factors. In most instances, the formulations evaluated do not adversely affect the film forming characteristics of the modified polyvinyl alcohol compositions of this invention. The aqueous moisture barrier-allantoin compositions of the invention generally have a lotion consistency and may be in the form of oil-in-water, water-in-oil or multiple emulsions. The lotions are preferably made by first preparing the oil phase then preparing the water phase and thereafter adding the water phase to the oil phase. Usually the aqueous phase is heated to a temperature of about 70° to about 80° C. and then added slowly with stirring to the oil phase which is heated to about the same temperature.

The oil phase components may contain a variety of materials including emulsifiers, emollients, oils, waxes, perfumes, lanolins, polyalkylenes, stearols and the like.

Water phase components may contain many different materials which include humectants, modified allantoin containing moisture barrier components of the invention, proteins and polypeptides, preservatives, alkaline agents, thickening agents, perfumes, stabilizers and antiseptics.

The lotions and ointments of the invention contain as an essential ingredient from 0.1-15% by weight and preferably from 0.5-5% by weight of the above described modified polyvinyl alcohol polymers of the invention. They may be added as aqueous dispersions containing 0.1-30% by weight of modified PVA or as dry powder.

The lotions may contain an emulsifier in an amount of from about 0.05 to about 8% and preferably from about 0.25 to about 5% to emulsify the oil components. Typical emulsifiers are selected from the group consisting of polyethoxylated fatty acids having less than about 30 mols of ethylene oxide per mol of fatty acid, ethoxylated esters, unethoxylated sugar esters, polyoxy-ethylene fatty ether phosphates, fatty acid amides, phospholipids, polypropoxylated fatty ethers, acyllactates, polyethoxylated poly-oxypropylene glycols, polypropoxyated polyoxyethylene glycols, polyoxyethylene, polyoxypropylene ethylene diamines, soaps and mixtures thereof.

Examples of such emulsifiers include polyoxyethylene (8) stearate, myristyl ethoxy (3) myristate, myristyl ethoxy (3) palmitate, methyl glucose sesquistearate, sucrose distearate, sucrose laurate, sorbitan monolaurate, polyoxyethylene (3) oleyl ether phosphate, polyoxyethylene (10) oleyl ether phosphate, lauric diethenyl amide, stearic monoethyl amide, lecithin, lanoline alcohol propoxylates, sodium stearoyl-2-lactate, calcium stearoyl-2-lactate, and the Pluoronics ® offered by BASF Wyandotte. Soaps such as alkaline metal or triethanolamine salts of long chain fatty acids which include sodium stearate, triethanolamine stearate and similar salts of lanolin fatty acids. A preferred emulsifier is polyoxyethylene (21) stearyl ether.

The lotion formulations may contain an emollient material in an amount ranging from 0.2 to 25% and more often 1 to 8% by weight. One function of the emollient is to ensure that the modified polyvinyl alcohol polymer is classified sufficiently to allow it to be in a film-like state on the surface of the skin. Typical emollients are selected from the group consisting of fatty alcohols, esters having fewer than about 24 carbon atoms (for example, isopropylpalmitate), branch chain esters having greater than about 24 total carbon atoms (for example, cetearyl octonate), squalane, liquid or solid paraffins, mixtures of fatty acids and squalane, mixtures of fatty acids and liquid or solid paraffins and mixtures thereof. Typical alcohols and fatty acids which are useful include those having from 12 to 22 carbon atoms such as cetyl alcohol, myristyl alcohol, stearyl alcohol, stearic acid and palmitic acid. Paraffins include, for example, mineral oil, petrolatum and paraffin wax.

The lotions and ointments are particularly stable and effective when adjusted to a pH of 6-8.

The following formulations will serve to demonstrate but not limit the formulations containing the modified polyvinyl alcohol film forming moisture barrier polymer of the invention. Typical lotions contain 0.1-5.0% of the above described modified PVA polymers, 2-5% of a fatty alcohol, and 2-5% emulsifier in an aqueous emulsion.

EXAMPLE A

A portion of the aqueous solution prepared according to Example 1 containing 0.5 grams of modified PVA polymer was diluted with water and added to an aqueous solution containing 2.4 grams cetyl alcohol, 1.6 grams stearyl alcohol and 3.0 grams of polyoxyethylene (21) stearyl ether (BRIJ ® 721 surfactant by ICI Americas Inc.). Additional water was added to bring the water concentration to 92.5%. After stirring for about five minutes at 75° C. the emulsion is permitted to cool to room temperature and stored. The lotion was tested subjectively for cosmetic elegance by applying the product to the back of the hand and arm. It was determined to have smooth, silky feel, drying time of less than 15 minutes and a film durability in excess of two days. Residual films and lotions are easily removed from the skin with soap and water.

As mentioned above the polymers of the invention had advantageous cosmetic properties that permit them to be used in preparing cosmetic formulations either as ready to use compositions or concentrates which have to be diluted before use. Therefore, the cosmetic formula may contain the modified polyvinyl alcohol polymers in concentrations ranging from 0.01-15% by weight. The solution of these polymers are particularly useful when they are applied to hair, either alone or with other active substances during a treatment such as shampooing, dyeing, setting, blow drying, permanent waving, etc. They may improve notably the quality of the hair. When employed in hair treatment they facilitate untangling of wet hair and do not remain on dry hair as a sticky residue. In some instances they are expected to give dry hair additional life, a soft feel, a glossy appearance and resistance to tangling.

Hair treating formulations containing dilute aqueous, alcohol or dilute alcohol solutions of the modified polyvinyl alcohol polymer can be employed. Furthermore, they may be employed as creams, lotions, gels or as aerosol sprays. They may be used in combination with perfumes, dyes, preserving agents, sequestering agents, thickening agents, emulsifying agents, etc.

EXAMPLE B

A typical hair rinse formulation containing 5 grams of the modified polymer of Example 1, 7 grams cetyl alcohol, 3 grams of a linear polyoxyethylenated $C_{10}-C_{18}$ fatty alcohol, 2 grams of a casein derivative, 0.5 grams tetradecyltrimethylammonium chloride and 82.5 grams of water and a minor amount of hair dye can be used to treat hair having improved looks and antistatic properties.

EXAMPLE C

A typical oxidation hair dye solution containing a 2.5 gram of the modified polymer of Example 2, 10 grams benzyl alcohol, 20 grams oleic acid, 3 grams polyoxyethylene (30), oleo cetyl alcohol, 7 grams oleic diethanolamide, 7.5 grams 2 octyldo-decanol, 2.5 grams triethanolamine lauric sulfate, 10 grams ethanol, 18 milliliters aqueous ammonium, 1 gram n,n-bis(2-hydroxyethanol)paraphenylenediamine, 0.4 grams resorcin, 0.15 grams m-aminophenol, 0.4 grams alphanaphthol, 0.1 grams hydro-quinone, 0.24 grams ethylene diamine tetracetic acid, 1 mililiter sodium bisulfite, and water sufficient to make 100 grams is a typical ammonia oil composition for use as an oxidation hair dye when 130 grams of the solution is mixed with 30 grams of hydrogen peroxide bleach. After hair is treated with the material and allowed to stand for 30-40 minutes and thereafter rerinsed the hair is expected to untangle easily and have a silky touch.

The modified polyvinyl alcohol compositions of the invention may be employed to improve the elegance and stability of personal care products such as liquid and bar soaps, shaving creams, bath products, antiperspirants, sunscreens, cleansing creams and as a suspending agents for insoluble pigments and pharmaceutical actives. Improvement is generally realized when from 0.5-5% by weight of the compositions of this invention are employed in conventional formulations as hereinafter exemplified.

| Ingredient | % W/W |
|---|---|
| Example D | |
| Roll-On Antiperspirant | |
| Example 1 | 4.0 |
| Polyoxyethylene (21) stearylether | 0.76 |
| Polyoxyethylene (2) stearylether | 3.24 |
| Water (deionized) | 34.76 |
| Dowicil 200 ®. Dow Chemical | 0.1 |
| Al Zr tetrachlorohydrex-Gly, Rezol 36G, Reheis | 57.14 |
| Example E | |
| Aerosol Shave Cream | |
| Example 2 | 5.0 |
| Cetyl alcohol | 4.3 |
| Polyoxyethylene (21) stearylether | 2.2 |
| Sorbic Acid | .17 |
| Water | 74.9 |

| Ingredient | % W/W |
|---|---|
| Fragrance | .08 |
| Water | 13.35 |
| Example F | |
| Oil-in-Water Sunscreen Lotion | |
| Mineral oil | 18.8 |
| Cetyl alcohol | 5.0 |
| Arlocel 60 ® emulsifier | 2.5 |
| Tween 60 ® emulsifier | 7.5 |
| Amyl para-diethylaminobenzoic acid | 1.2 |
| Example 1 | 2.0 |
| Water | 63.0 |
| Preservative | q.s. |
| Example G | |
| Water-in-Oil Pigmented Makeup | |
| Mineral Oil | 10 |
| Beeswax | 1.5 |
| Cevesin wax | 1.0 |
| Arlacel 186 ® emulsifier | 3.2 |
| Sorbo ® sorbitol | 28.8 |
| TiO$_2$ and other pigments | 20.0 |
| Water | 33.5 |
| Example 2 | 2.0 |
| Example H | |
| Calamine Lotion | |
| Calamine | 80 gms |
| Zinc Oxide | 80 gms |
| Glycerine | 20 mls |
| Bentonite magma | 250 mls |
| Calcium hydroxide (concentrated aqueous sol.) | 950 mls |
| Example 1 | 50 gms |

What is claimed is:

1. An aqueous dispersion comprising from 0.1-30 percent by weight of a quaternary nitrogen modified polymer which comprises a polyvinyl alcohol base chain having a number average molecular weight of 2,000-1,000,000 having pendant groups of the formula:

$$-RN^+R_1R_2R_3A^-$$

wherein:
R is selected from the group consisting of alkylene, alkyl substituted alkylene, hydroxy alkylene, oxylinked alkylene, sulfur linked alkylene, and nitrogen linked alkylene radials wherein such total substituent has a formula weight of 14 to about 3,000;
$R_1$, $R_2$ and $R_3$ are independently selected from the group consisting of hydrogen, alkyl and arylakyl radicals having 1-22 carbon atoms;
$A^-$ is an anion selected from allantoin anions and derivative thereof.

2. The dispersion of claim 1 wherein R is a radical selected from the group consisting of —CH$_2$—CHOH—CH$_2$— and $$-_nCH_2CH(OH)CH_2-$$

wherein $R_1$, $R_2$ and $R_3$ are independently selected from the group consisting of alkyl and arylalkyl radicals having 1-20 carbon atoms and n=1-20.

3. The dispersion of claim 2 wherein said pendant group is —COCH$_2$N$^+$R$_1$R$_2$R$_3$A$^-$.

4. The dispersion of claim 2 wherein $R_1$, $R_2$ and $R_3$ are selected from the group consisting of —CH$_3$, —CH$_2$CH$_3$, —CH$_2$CH$_2$CH$_3$, $$-\underset{\underset{CH_3}{|}}{CH}-CH_3,$$

and —CH₂Ph where Ph is phenyl.

5. The dispersion of claim 3 wherein $R_1$, $R_2$ and $R_3$ are selected from the group consisting of —CH₃, —CH₂—CH₃, —CH₂CH₂CH₃,

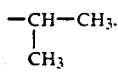

and —CH₂Ph where Ph is phenyl.

6. The dispersion of claim 2 wherein $R_1$, $R_2$ and $R_3$ are methyl groups and the nitrogen content of said base chain ranges from 0.01-3% by weight.

7. The dispersion of claim 4 wherein $R_1$, $R_2$ and $R_3$ are methyl groups and the nitrogen content of said base chain ranges from 0.1 to 3% by weight.

8. The dispersion of claim 2 made by mixing allantoin with the product prepared by the steps of (a) reacting equimolar quantities of epichlorohydrin with aqueous trimethylamine at temperatures below 25° C. and (b) reacting at 40°-90° C. the aqueous product of step (a) with an aqueous dispersion of polyvinyl alcohol having a number average molecular weight of at least 2,000 containing catalytic quantities of base.

9. The dispersion of claim 2 made by mixing allantoin with the product made by reacting (chlorohydroxypropyl)trialkylammonium chloride in aqueous solution or crystalline form with an aqueous solution of polyvinyl alcohol having a number average molecular weight of at least 2,000, said solution containing catalytic quantities of potassium hydroxide, and maintaining the resulting reaction mixture at 40°-90° C.

10. The dispersion of claim 2 made by mixing allantoin with the product made by reacting an aqueous dispersion of polyvinyl alcohol polymer having a number average molecular weight of at least 2,000 with an aqueous solution of 2,3-epoxypropyl trialkylammonium halide, said reaction being carried out at a temperature of 40°-90° C. in the presence of a catalytic amount of base in amounts wherein the mol ratio of said ammonium halide to each mol of hydroxyl group on the polyvinyl alcohol polymer ranges from 0.003-1.

11. The dispersion of claim 2 made by mixing allantoin with the product made by reacting an aqueous dispersion of polyvinyl alcohol polymer having a number average molecular weight of at least 2,000 with an aqueous solution of 2,3-epoxypropyltrialkylammonium halide at a temperature of 40°-90° C. in the presence of a catalytic amount of acid in amounts wherein the mol ratio of said ammonium halide to each mol of hydroxyl group on the polyvinyl alcohol polymer ranges from 0.003-1.

12. The dispersion of claim 2 made by mixing allantoin with the product made by reacting 2, 3-epoxypropyltrimethylammonium chloride in aqueous solution or crystalline form with an aqueous dispersion of polyvinyl alcohol having number average molecular weight ranging from 2,000-200,000 and a random distribution of oxygen linked pendant groups having a general formula:

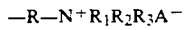

wherein R is selected from the group consisting of an alkylene, a substituted alkylene, or acylene radical, 13. The dispersion of claim 2 made by reacting 2 3-epoxypropytrimethylammonium chloride in aqueous solution with an aqueous dispersion of polyvinyl alcohol having a number average molecular weight of at least 2,000, said reaction being carried out at a temperature of 40°-90° C. in the presence of a catalytic amount of base in amounts wherein the mol ratio of said ammonium halide to each mol of hydroxyl group on the polyvinyl alcohol polymer ranges from 0.003-1.

14. The dispersion of claim 2 prepared by reacting polyvinyl alcohol, having a number average molecular weight of at least 2,000 with trimethylethoxycarbonylmethylammonium halide in dipolar aprotic solution to which catalytic quantities of manganese acetate are added, said reaction being carried out at a temperature of 100°-150° C. for about 5-8 hours.

15. The dispersion of claim 2 made by mixing allantoin with the product made by a process wherein benzyldimethylethoxycarbonylmethylammonium halide in aqueous solution or crystalline form is added to an aqueous dispersion of polyvinyl alcohol containing catalytic quantities of potassium hydroxide and maintaining said resulting mixture at 40°-90° C. until reaction is complete.

16. The dispersion of claim 2 which is separated from an aqueous reaction mixture by precipitation through the addition of a nonsolvent selected from the group consisting of acetone and methanol.

17. The dispersion of claim 2 which is purified by dialysis or ultrafiltration.

* * * * *

UNITED STATES PATENT AND TRADEMARK OFFICE
CERTIFICATE OF CORRECTION

PATENT NO. : 5,112,886
DATED : May 12, 1992
INVENTOR(S) : Charalambos J. Phalangas It is certified that error appears in the above-identified patent and that said Letters Patent is hereby corrected as shown below:

Column 16, line 55, (claim 2) should read as follows;

$$-[(CH_2CH(CH_2N^+R_1R_2R_3A^-)O]_n CH_2CH(OH)CH_2-$$

Column 17, line 14, (claim 7) "The dispersion of claim 4" should read as --The dispersion of claim 3--

Col. 18, lines 18-19 (claim 13)
"2 3-epoxypropytrimethylammonium chloride" should read as --2,3-epoxypropyltrimethylammonium chloride--

Signed and Sealed this

Third Day of August, 1993

Attest:

MICHAEL K. KIRK

*Attesting Officer*   *Acting Commissioner of Patents and Trademarks*